(12) United States Patent
Auld

(10) Patent No.: US 6,634,799 B2
(45) Date of Patent: Oct. 21, 2003

(54) ADAPTER FOR COUPLING A BNC CONNECTOR TO AN SMA BUSHING

(75) Inventor: Michael D. Auld, Chesterfield, MO (US)

(73) Assignee: Synergetics, Inc., St. Charles, MO (US)

( * ) Notice: Subject to any disclaimer, the term of this patent is extended or adjusted under 35 U.S.C. 154(b) by 0 days.

(21) Appl. No.: 10/092,710

(22) Filed: Mar. 7, 2002

(65) Prior Publication Data

US 2002/0094727 A1 Jul. 18, 2002

Related U.S. Application Data

(63) Continuation-in-part of application No. 09/542,660, filed on Apr. 4, 2000, now Pat. No. 6,357,932.

(51) Int. Cl.[7] .................................................. G02B 6/36
(52) U.S. Cl. ........................... 385/76; 385/56; 385/138; 385/88
(58) Field of Search ............................... 385/53, 55, 56, 385/60, 66, 70, 76, 81, 92, 88, 138, 139; 439/578, 585, 638, 651, 675

(56) References Cited

U.S. PATENT DOCUMENTS

| 3,932,761 | A | * | 1/1976 | Ramsey et al. ............. 250/552 |
| 4,199,736 | A |   | 4/1980 | McTaggart et al. |
| 4,553,814 | A |   | 11/1985 | Bahl et al. |
| 4,902,094 | A | * | 2/1990 | Shank ........................ 385/55 |
| 5,074,637 | A |   | 12/1991 | Rink |
| 5,085,492 | A |   | 2/1992 | Kelsoe et al. |
| 5,452,391 | A |   | 9/1995 | Chou et al. |
| 5,570,445 | A |   | 10/1996 | Chou et al. |
| 5,785,645 | A |   | 7/1998 | Scheller |
| 5,807,242 | A |   | 9/1998 | Scheller et al. |

* cited by examiner

Primary Examiner—Hemang Sanghavi
Assistant Examiner—Scott A Knauss
(74) Attorney, Agent, or Firm—Thompson Coburn, LLP

(57) ABSTRACT

An assembly used to adapt a BNC type connector of a microsurgical optic fiber instrument to a threaded SMA type bushing of a light source includes an adapter that can be threaded on the bushing of the light source and is also connectable to the BNC connector.

20 Claims, 4 Drawing Sheets

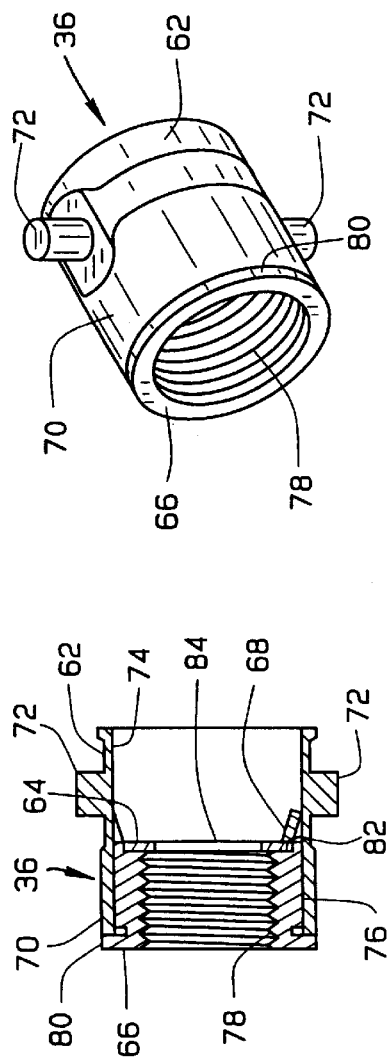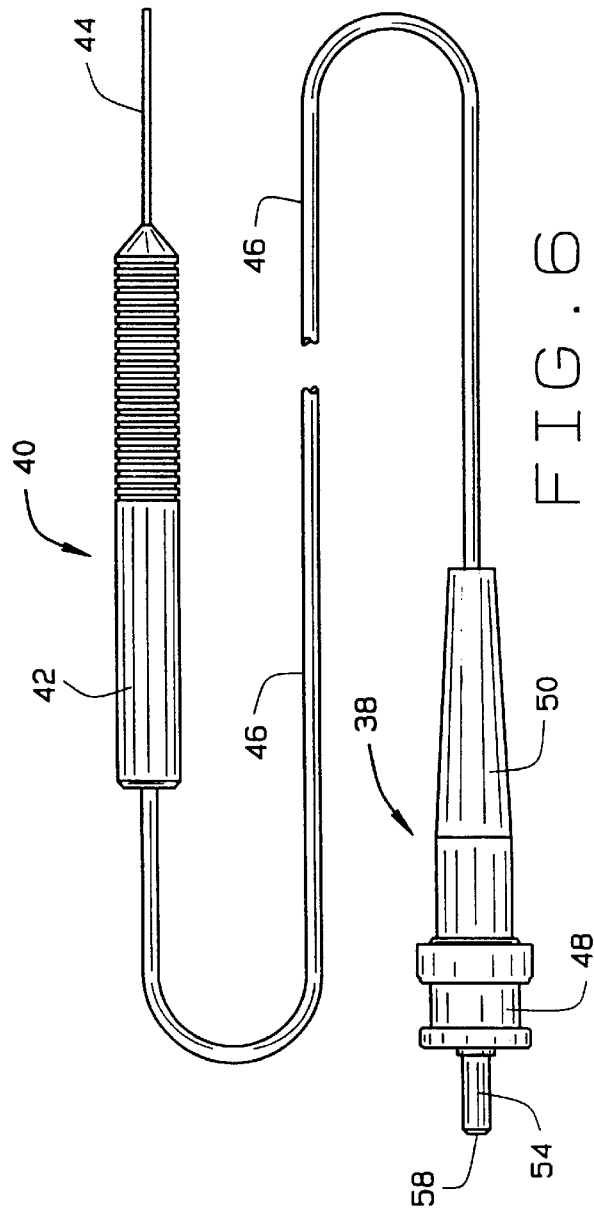

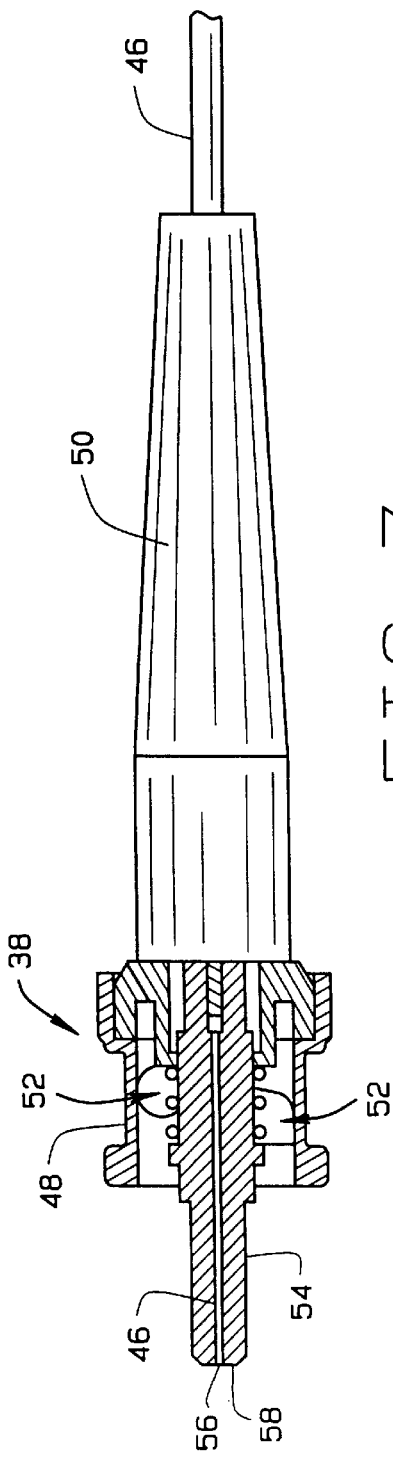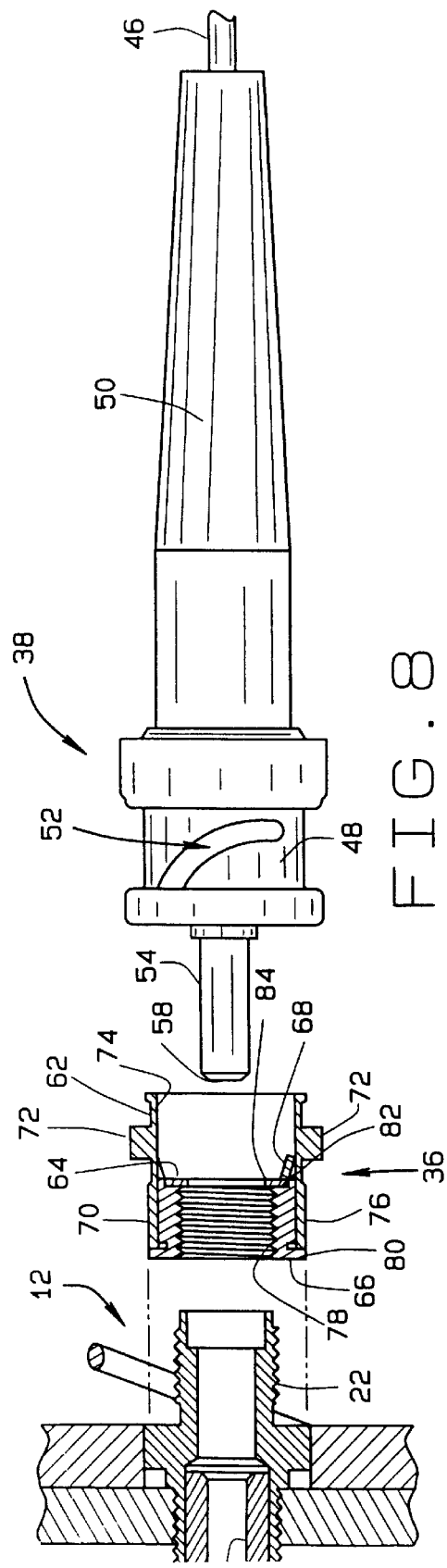

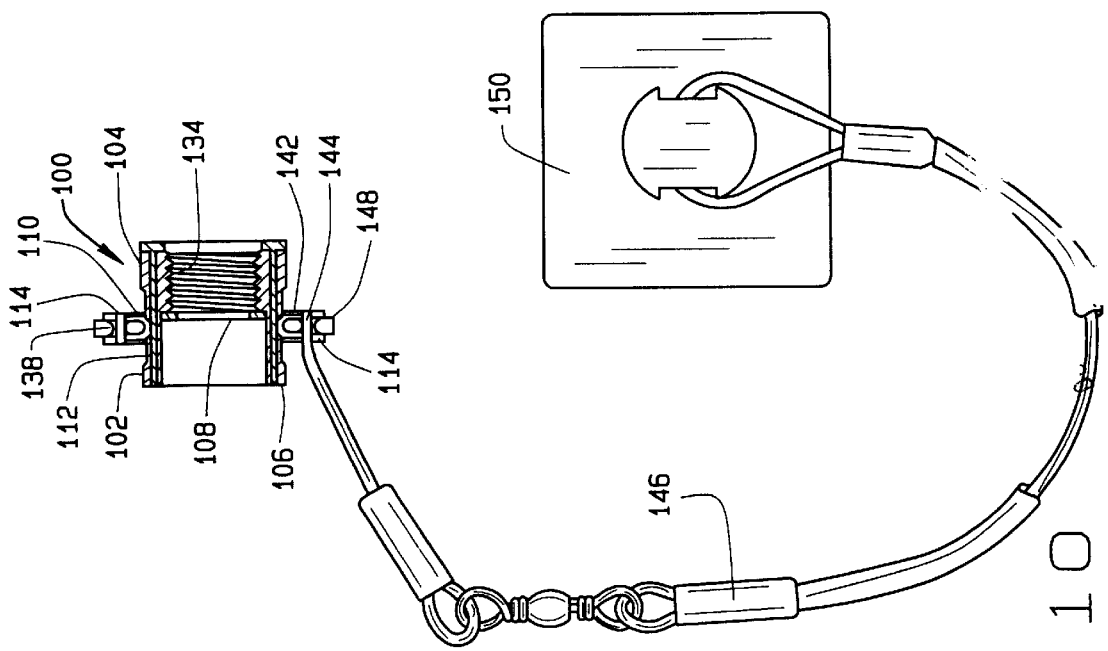
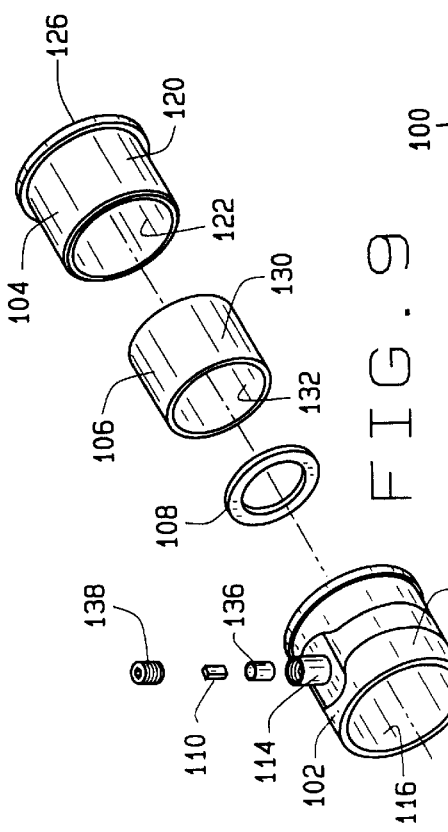
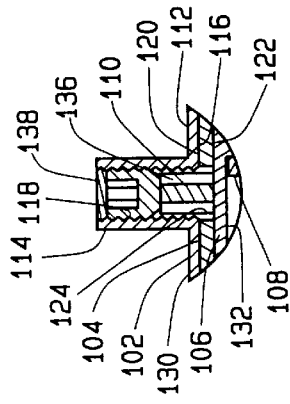
FIG. 9
FIG. 11
FIG. 10
FIG. 12

ADAPTER FOR COUPLING A BNC CONNECTOR TO AN SMA BUSHING

This is a Continuation-in-Part Patent Application of application Ser. No. 09/542,660, filed Apr. 4, 2000 U.S. Pat. No. 6,357,932.

BACKGROUND OF THE INVENTION (1) Field of the Invention

The present invention pertains to an assembly that is used to adapt a BNC type connector of a microsurgical optic fiber instrument to a threaded SMA type bushing connector of a light source.

(2) Description of the Prior Art

In microsurgery such as ophthalmic surgery or surgery of the eye, various different types of instruments are available for use by the surgeon to deliver light to the interior of the eye. These instruments deliver light for illumination as well as laser light for use in surgery. A basic microsurgical instrument of this type is comprised of a handle with a projecting tubular probe or tip and a length of optic fiber entering the rearward end of the handle and passing through the handle and the tip to the tip distal end. The proximal end of the optic fiber opposite its connection to the handle is provided with a connector for connecting the fiber proximal end to a light source, either an illumination source or a laser light source. By positioning the proximal end of the optic fiber adjacent the light source, the light is transmitted through the fiber to its distal end and is emitted from the distal end. Where the light source is a source of laser light used in eye surgery, the positioning of the fiber proximal end relative to the laser light must be accurately controlled. Connectors employed for such a purpose are referred to as SMA type connectors.

FIGS. 1 and 2 show examples of prior art SMA connectors with FIG. 1 illustrating the construction of a male optic fiber connector and FIG. 2 illustrating the construction of a female optic fiber connector. These prior art connectors are widely used and will only be described generally.

The female connector or bushing 12 is provided with an alignment sleeve 18 in its interior that ensures a precise alignment of an optic fiber (not shown) extending through the male connector 10 along the male connector center axis 14. A laser light source is positioned relative to the female connector 12 to direct a beam of laser light along the female connector center axis 16. The female connector has a first set of external screw threading 20 that is employed in securing the female connector 12 to a wall or bracket of the laser light source to securely hold the female connector relative to the light source. A second set of external screw threading 22 on the female connector is employed in attaching the male connector 10 to the female connector.

The male connector 10 includes a center ferrule 24 on which a cable nut 26 is mounted for rotation. The cable nut 26 is secured on the ferrule 24 by a back post 28 that is screw threaded on the ferrule. The cable nut 26 has internal screw threading 30 that is complementary to the external screw threading 22 of the female connector. The optic fiber of the microsurgical instrument (not shown) passes through the back post 28 and the ferrule 24 with a distal end of the optic fiber being positioned adjacent the distal end of the ferrule 24.

In attaching the male connector 20 to the female connector 12, the ferrule 24 is first inserted through the interior bore of the female connector and into the alignment sleeve 18. The cable nut 26 is turned causing its internal threading 30 to be screw threaded onto the external threading 22 of the female connector and to securely connect the male connector 10 with the female connector 12 with their respective axes aligned. In this way, the beam of laser light of the light source (not shown) is directed at the exposed end of the optic fiber contained in the male connector 10.

Use of the prior art connectors described above has been found to be inconvenient in that it is necessary to completely unscrew the cable nut 26 of the male connector 10 from the external screw threading 22 of the female connector 12 when removing one instrument from the light source and then screw a cable nut 26 of another instrument onto the female connector external threading 22 when switching one microsurgical instrument for another. It would be more convenient if the male connector 10 could be quickly connected with and disconnected from the female connector 12 without requiring repeated rotations of a cable nut in connecting and disconnecting the two connectors.

The prior art also includes laser light sources having female connectors 12 and sets of microsurgical instruments having male connectors 10 that can only be used with each other. This has been found to be inconvenient when it is desirable to use other types of microsurgical instruments with the particular laser light source. The prior art laser light source is specifically designed so that it will not operate if a male connector of a microsurgical instrument is connected to the light source where the microsurgical instrument and male connector are not manufactured by the particular manufacturer of the light source. This is accomplished by encoding the male connector 10 of the surgical instrument with an electronic device that is recognized by the light source when the male connector is attached to the female connector of the light source. An example of such a male connector and female connector is disclosed in the U.S. Pat. No. 5,085,492 of Kelsoe et al.

The above-described inconvenience could be overcome by an adapter that can be attached to the female connector of a laser light source of the type that operates only with associated electronically encoded surgical instruments where the adapter contains the electrical device recognized by the light source and also enables a quick connect and disconnect of the surgical instrument to the adapter.

SUMMARY OF THE INVENTION

The present invention overcomes the inconveniences of prior art SMA type connectors described above by providing an adapter that enables a BNC type connector to be attached to the external screw threading of a female connector or bushing of the SMA type. In addition, the adapter also is electronically encoded and therefore enables use of any type of surgical instrument having a BNC type connector with a laser light source of the type that only recognizes electronically encoded surgical instruments.

The adapter of the invention is part of an assembly that includes a microsurgical optic fiber instrument having a BNC type connector in lieu of a SMA type connector usually found on these types of surgical instruments. Like the SMA connector, the BNC connector also has a center ferrule that projects from the connector and through which the optic fiber extends. However, instead of having the cable nut found on SMA connectors, the BNC connector of the invention has a conventional BNC type connector including a cylindrical collar with a pair of spiraling slots formed in the collar.

The adapter includes a cylindrical adapter sleeve constructed of a conductive material, preferably metal. The sleeve has an external surface with a pair of posts projecting from the surface on diametrically opposite sides of the sleeve. The posts are positioned to be engaged by the slots of the BNC connector to enable the BNC connector to be attached to the exterior surface of the sleeve by merely turning the BNC connector one quarter turn relative to the sleeve. The sleeve also has a cylindrical interior surface and a cylindrical insulator is secured inside the sleeve. In one embodiment of the adapter the insulator does not extend through the entire length of the sleeve but is only positioned adjacent the end of the sleeve to be attached to the externally threaded female bushing of the laser light source of the type described earlier. The insulator has internal screw threading that is complementary to that of the female bushing of the laser light source. Screwing the insulator threading onto the external threading of the light source female bushing attaches the sleeve to the light source female bushing but insulates the conductive material of the sleeve from that of the bushing.

An annular conductive stop is also secured in the interior of the adapter sleeve. The stop is positioned in the adapter sleeve where it will come into electrical contact with the female bushing of the laser light source when the adapter sleeve is attached to the female bushing.

An electrical device is also secured to the interior of the adapter sleeve. The electrical device is connected electrically between the annular stop and the interior surface of the sleeve, thus establishing a circuit path from the annular stop to the sleeve through the electrical device.

A second, preferred embodiment of the adapter also includes the cylindrical adapter sleeve having an external surface with a pair of posts projecting from the surface as in the first embodiment. The posts are positioned to be engaged by the slots of the BNC connector as in the first embodiment. The sleeve has a cylindrical interior surface. The sleeve of the second embodiment differs from that of the first embodiment in that at least one of the sleeve posts has an internally threaded bore extending entirely through the post from the exterior of the sleeve to the interior of the sleeve.

A cylindrical insulator is secured inside the sleeve bore. The insulator differs from that of the first embodiment in that it extends entirely through the length of the sleeve. A hole is provided through the insulator and is aligned with the threaded interior bore of the sleeve post.

A conductive cylindrical insert is provided in the interior bore of the insulator. The insulator separates and insulates the insert from the sleeve. The insulator has internal screw threading that is complementary to that of the female bushing of the laser light source. The internal screw threading does not extend through the entire length of the insert, but is only positioned adjacent the end of the insert to be attached to the externally threaded female bushing of the laser light source. An annular conductive stop is also secured in the interior of the insert. The stop is positioned at the end of the insert internal screw threading where it will come into electrical contact with the female bushing of the laser light source when the adapter sleeve is attached to the female bushing.

An electrical device is also secured to the interior of the adapter sleeve. However, in this embodiment the electrical device is positioned inside the sleeve post interior bore and is connected electrically between the conductive insert and the sleeve post, thus establishing a circuit path from the insert to the sleeve through the electrical device. In both embodiments of the adapter, the electrical device is preferably a resistor. However, other electrical devices as well as combinations of electrical devices may be employed in lieu of the resistor.

In use of either of the embodiments of the assembly, the adapter sleeve is first attached to the external threading of the laser light source female bushing by screw threading the insulator of the first embodiment or the insert of the second embodiment onto the female bushing until the end of the female bushing comes into contact with the annular stop inside the sleeve. This establishes a circuit path from the female bushing through the electrical device and the conductive sleeve of the adapter. With the adapter attached to the female bushing of the laser light source, any optic fiber microsurgical instrument having the BNC connector of the invention may be easily connected and disconnected from the laser light source by turning the BNC connector one quarter turn relative to the adapter attached to the laser light source.

When the BNC connector of the surgical instrument is attached on the adapter, an electric circuit is established from the female bushing of the laser light source through the electrical device, the adapter and now the collar of the BNC connector. The prior art laser light source discussed above also includes an external contact that is positioned to come into contact with the cable nut of a conventional SMA type connector when attached to the female bushing of the light source. This external contact comes into contact with the BNC connector of the assembly and thereby a complete electrical circuit is established from the female bushing of the light source through the electrical device of the adapter and through the BNC connector and the external contact of the light source.

The electrical device, for example the resistor referred to, is specifically chosen to make either adapter compatible with the particular light source. When the electric circuit discussed above is established by connecting the adapter and BNC connector of the invention with the female bushing of the light source, the light source recognizes the particular electrical device provided in the adapter. Thus, the laser light source will operate as though an SMA connector manufactured by the same manufacturer of the light source was connected to the female bushing of the light source.

Thus, the assembly of the invention including the adapter and the BNC connector enables a quick connect and disconnect of the surgical instrument with the laser light source and also enables surgical instruments to be employed with the particular light source that were not manufactured by the particular manufacturer of the light source.

DETAILED DESCRIPTION OF THE DRAWINGS

Further objects and features of the invention will be revealed in the following detailed description of the preferred embodiment of the invention and in the drawing figures wherein:

FIG. 4 is a side-sectioned view of the adapter of the invention;

FIG. 5 is a perspective view of the adapter of the invention;

FIG. 6 is side view of a microsurgical instrument employing a BNC type connector of the invention;

FIG. 7 is a side partially sectioned view of the BNC connector of the invention shown in FIG. 6;

FIG. 8 is a side view illustrating the attachment of the adapter of the invention onto the female bushing of a laser light source and the attachment of the BNC connector of the invention to the adapter;

FIG. 9 is a perspective, exploded view of a second embodiment of the adapter of the invention;

FIG. 10 is a side-sectioned view of the second embodiment of the adapter of the invention;

FIG. 11 is a perspective view of the second embodiment of the adapter of the invention; and FIG. 12 is a partial, cross section view of the details of the sleeve interior.

DESCRIPTION OF THE PREFERRED EMBODIMENT

Figure 1:
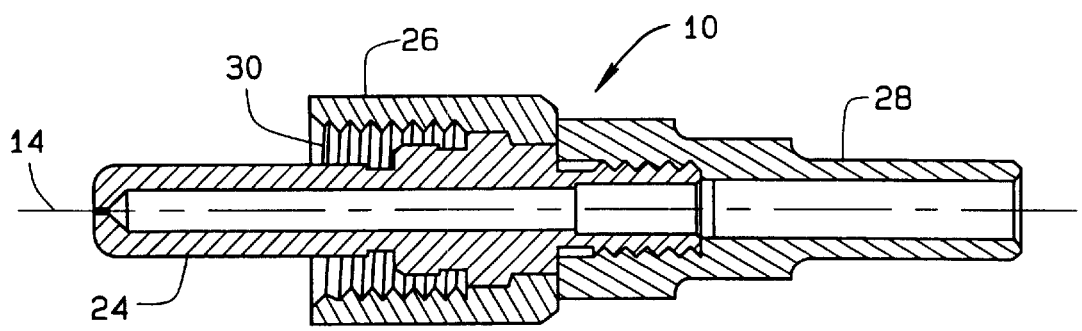
FIG. 1 is a side-sectioned view of a prior art SMA type male connector employed with optic fiber microsurgical instruments.
Figure 2:
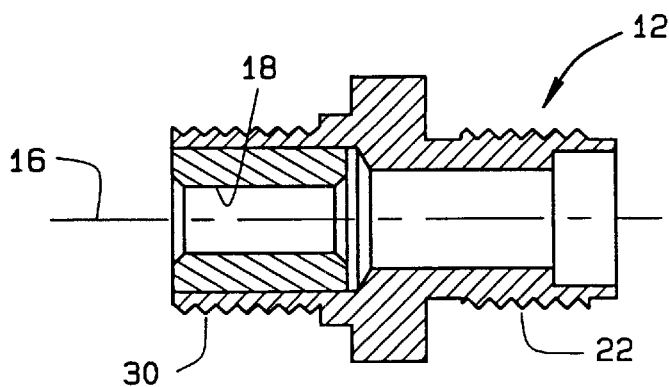
FIG. 2 is a side-sectioned view of a prior art female connector employed with the male connector of FIG. 1.

The assembly of the invention includes an adapter 36 and a BNC connector 38 for a microsurgical optic fiber instrument 40 that transmits laser light used in surgery. Alternatively, the optic fiber instrument could be employed to provide illumination to a surgical site. The adapter 36 enables the BNC connector 38 to be attached to the external screw threading of a female connector or bushing of the SMA type employed on a laser light source such as that disclosed in the earlier references U.S. Pat. No. 5,085,492. The adapter 36 also enables the microsurgical instrument 40 to be quickly and easily connected to and disconnected from the bushing without repeatedly rotating the connector to screw it on or unscrew it from the bushing as is required by prior art SMA instrument connectors. In addition, the adapter is also electrically encoded and enables use of any type of surgical instrument having a BNC type connector with a laser light source of the type that only recognizes electrically encoded surgical instruments.

The surgical instrument 40 and the BNC connector 38 of the invention are shown in FIG. 6. In this illustrative embodiment of the invention, the surgical instrument 40 is a laser probe. The construction of the surgical instrument is, for the most part, conventional and will only be described briefly. The instrument includes a handle 42 having a bore passing axially through its center. A tubular metal tip 44 or probe is secured to one end of the handle and communicates with the handle interior bore. An optic fiber 46 protected by an external layer of cladding extends into the handle bore at the opposite end of the handle from the tip 44. In the handle 42, the cladding is removed from the optic fiber and only the optic fiber extends through the tip 44 to a distal end of the fiber adjacent the distal end of the tip. The opposite end of the optic fiber extends into the BNC connector 38 of the invention.

The BNC connector 38 is basically a conventional BNC connector that is typically used as an electronic connector. Because the construction of the BNC connector is, for the most part, conventional, it will not be described in detail. The connector includes a cylindrical collar 48 that is mounted on a body 50 of the connector for rotation relative thereto. The collar 48 is constructed of a conductive material. The collar includes a pair of diametrically opposite grooves or slots 52. The slots 52 spiral around the collar 48 for one quarter of the circumference of the collar. A center ferrule 54 projects from the connector 38 through the center of the collar 48. The exterior of the ferrule 54 is dimensioned to fit tightly in the alignment sleeve 18 of the female connector or bushing 12 of the laser light source (not shown). The BNC connector 38 differs from prior art BNC connectors in that the optic fiber 46, with the cladding removed, extends through the center of the connector ferrule 54 with the proximal end 56 of the optic fiber being positioned adjacent the end 58 of the ferrule. Thus, with the ferrule securely inserted in the alignment sleeve 18 of the female connector 12 of the light source, the proximal end of the optic fiber 56 is accurately positioned relative to the laser light source.

Figure 3:
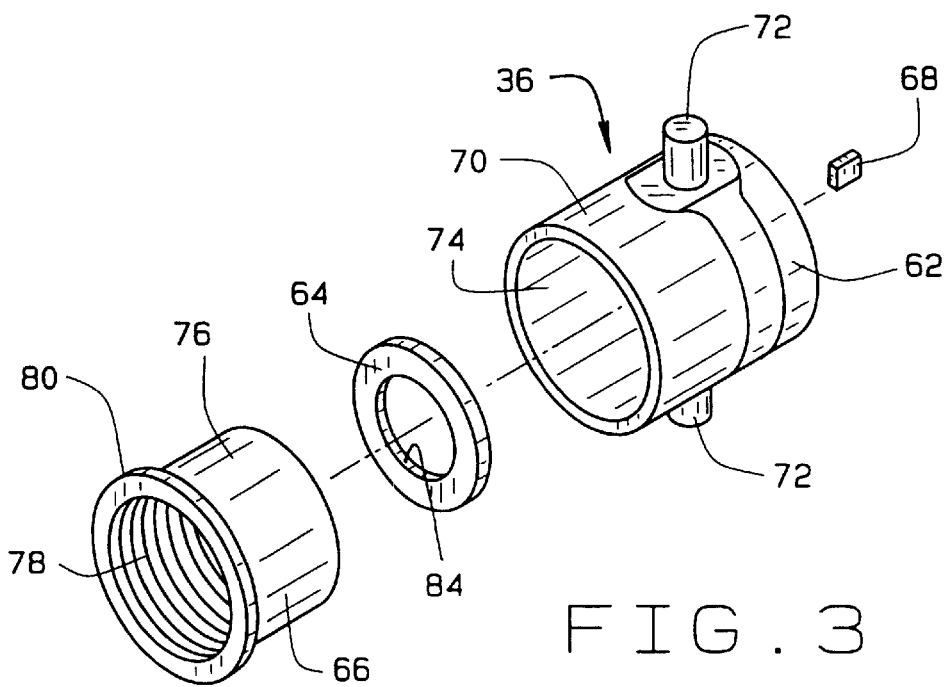
FIG. 3 is a perspective, exploded view of the adapter of the invention.

The adapter 36 of the invention is shown in FIGS. 3–5. The adapter is basically comprised of a cylindrical conductive sleeve 62, an annular conductive stop 64, a cylindrical insulator 66 and an electronic device 68, in the illustrated embodiment a resistor 68.

The adapter sleeve 62 has an external surface 70 that is dimensioned to fit inside the cylindrical collar 48 of the BNC connector 38 and engage in electrical contact therewith. A pair of posts 72 project from the sleeve external surface 70 on diametrically opposite sides of the sleeve. The posts 72 are positioned on the sleeve to engage in the pair of slots 52 of the BNC connector collar 48 when attaching the connector to the adapter. The engagement of the posts 72 in the adapter collar slots 52 enables the BNC connector 38 to be attached on the external surface 70 of the adapter by merely rotating the BNC connector one quarter turn. Thus, the BNC connector 38 can also be disconnected from the external surface of the adapter 36 by turning the BNC connector one quarter turn in the opposite direction. The sleeve also has a cylindrical interior surface 74 surrounding an internal bore of the sleeve.

The insulator 66 is cylindrical and has an external surface 76 dimensioned to fit tightly into the internal surface 74 of the sleeve. The insulator 66 is constructed of an insulating material. The interior surface of the insulator is provided with internal screw threading 78 that is complementary to the external screw threading 22 of the female connector 12 of the laser light source. One end of the insulator has a circular flange 80 that engages against the end of the adapter sleeve 62 when inserting the insulator into the adapter. The opposite end of the insulator has an annular recessed shoulder 82. The insulator 66 is inserted into the interior of the adapter sleeve 62 at the end of the sleeve opposite the pair of posts 72 as shown in FIGS. 3 and 4. The insulator is secured in place by an epoxy or by other equivalent means.

The annular stop 64 is basically a circular brass washer that is dimensioned to fit inside the annular recessed shoulder 82 of the insulator as shown in FIG. 4. The stop has a circular inner surface 84 that is dimensioned slightly smaller than the interior diameter of the threaded bore 78 of the insulator. The brass stop 64 is conductive and is positioned to come into electrical contact with the end of the female bushing 12 of the laser light source when the adapter 36 is screw threaded onto the bushing. The stop 64 is secured in the recess 82 of the insulator by an epoxy or by other equivalent means.

The electrical device 68, in the preferred embodiment a resistor, is secured to the adapter sleeve interior surface 74 by an epoxy or other equivalent means. The device 68 is connected electrically with the annular stop 64 and the internal surface 74 of the adapter sleeve 62, thus creating an electric circuit between the annular stop 64 and the adapter sleeve 62. In alternative embodiments, the resistor of the electrical device 68 could be replaced with some other type of electrical device or a combination of electrical devices depending on what would be recognized by the light source the adapter is to be used with.

In use of the assembly illustrated in FIG. 8, the adapter sleeve 62 is first attached to the external threading 22 of the laser light source female bushing by screw threading the insulator 66 of the sleeve onto the female bushing until the end of the female bushing comes into contact with the annular stop 64 inside the sleeve. This establishes a circuit path from the female bushing 12 through the annular stop 64, the electrical device 68 and the conductive sleeve 62 of the adapter. With the adapter attached to the female bushing of the laser light source, any optic fiber microsurgical instrument having the BNC connector of the invention may be easily connected and disconnected from the laser light source by turning the BNC connector one quarter turn relative to the adapter attached to the laser light source.

When the BNC connector 38 of the surgical instrument is attached on the adapter 36, an electric circuit is established from the female bushing 12 of the laser light source through the annular stop 64, the electrical device 68, the adapter sleeve 62 and now the collar 48 of the BNC connector. The prior art laser light source discussed above also includes an external contact 88 that is positioned to come into contact with the cable nut of a conventional SMA type connector when attached to the female bushing of the light source. This external contact 88 comes into contact with the BNC connector 38 of the assembly and thereby a complete electrical circuit is established from the female bushing 12 of the light source through the electrical device 68 of the adapter and through the BNC connector 38 and the external contact 88 of the light source.

The second embodiment of the adapter 100 of the invention is shown in FIGS. 9–12. The adapter is basically comprised of a cylindrical conductive sleeve 102, a cylindrical insulator 104, a cylindrical conductive insert 106, an annular conductive stop 108 and an electronic device 110. In the illustrated embodiment of the second adapter 100 the electronic device 68 is a resistor. The second embodiment of the adapter 100 is designed to function in the same manner as the first described embodiment of the adapter 36. It is also designed to provide a quick connect and disconnect coupling between a BNC connector 38 of a surgical instrument and the female bushing 12 of a laser light source.

The adapter sleeve 102 has an exterior surface 112 that is dimensioned to fit inside the cylindrical collar 48 of the BNC connector 38 and engage in electrical contact therewith. A pair of posts 114 project from the sleeve exterior surface 112 on diametrically opposite sides of the sleeve. The posts 114 are positioned on the sleeve to engage in the pair of slots 52 of the BNC connector collar 48 when attaching the connector to the adapter. The engagement of the posts 114 in the adapter collar slots 52 enables the BNC connector 38 to be attached on the adapter exterior surface 112 by merely rotating the BNC connector one quarter turn. Thus, the BNC connector 38 can also be disconnected from the adapter exterior surface 112 by turning the BNC connector one quarter turn in the opposite direction. The sleeve 102 also has a cylindrical interior surface 116 surrounding an interior bore through the sleeve. Each of the sleeve posts 114 has an internally screw threading bore 118 extending completely through the post communicating the exterior of the sleeve with the sleeve interior bore.

The insulator 104 has an external surface 120 that is dimensioned to fit tightly into the interior surface 116 of the sleeve. The insulator 104 is constructed of an insulating material and is dimensioned to extend entirely through the interior bore of the sleeve 102. The insulator is provided with a cylindrical interior surface 122 surrounding an interior bore of the insulator. A hole 124 passes through the insulator between the exterior surface 120 and the interior surface 122. The hole 124 is positioned in alignment with one of the internally screw threaded bores 118 of the sleeve posts 114. One end of the insulator has an annular flange 126 that engages against an end of the adapter sleeve 102 when the insulator is inserted into the sleeve. The insulator hole 124 is formed through the insulator after it is inserted into the sleeve in order to align the insulator hole with the internally screw threaded bore 118 of one of the sleeve posts. The insulator 104 is secured in place in the interior bore of the sleeve 102 by an epoxy or by other equivalent means.

The cylindrical conductive insert 106 has an exterior surface 130 that is dimensioned to fit tightly into the interior surface 122 of the insulator. The insert 106 is constructed of an electrically conductive material and is dimensioned to extend the entire length of the insulator 104 and the sleeve 102. The insert has a cylindrical interior surface 132 with internal screw threading 134 formed on a portion of the interior surface. The internal screw threading 134 of the insert is complementary to the external screw threading 22 of the female connector 12 of the laser light source. The insert 106 is secured in place in the insulator 104 by an epoxy or by other equivalent means.

The annular stop 108 is basically a circular brass washer that is dimensioned to fit inside the interior bore of the cylindrical insert 106. The brass stop 108 is conductive and is positioned at the end of the internal screw threading 134 of the insert where it will come into electrical contact with the end of the female bushing 12 of the laser light source when the adapter 100 is screw threaded onto the bushing. The stop 108 is secured in the insert 106 against the internal screw threading 134 by brazing or by other equivalent means.

The electrical device 110, in the preferred embodiment a resistor, is secured to the adapter sleeve 102 inside one of the internally screw threaded bores 118 of the posts. Positioning the electrical device 110 inside the post of the sleeve provides better protection for the device than that provided by the first embodiment. As shown in FIG. 9 and in the detail of FIG. 12, the electronic device 110 is inserted into a cylindrical plastic bushing 136 and then is inserted into one of the interior bores 118 of the sleeve posts. The plastic bushing 136 properly positions the electrical device 110 in the post bore. One end of the electrical device 110 extends through the hole 124 of the insulator and makes electrical contact with the exterior surface 130 of the conductive insert. A set screw 138 is screw threaded into the internally screw threaded bore 118 of the post and makes electrical contact with the opposite end of the electronic device 110. With the set screw 138 screw threaded into the post bore 118 and contacting the electronic device 110, an electrical connection is established between the conductive insert 106, the electronic device 110, the set screw 138 and the post 114 and the exterior surface 112 of the sleeve. In alternate embodiments, the resistor of the electronic device 110 could be replaced with some other type of electrical device or a combination of electrical devices depending on what would be recognized by the light source the adapter is to be used with.

In the opposite post 118 from that containing the electronic device 110, a first set screw 142 is screw threaded into the internally screw threaded bore 118 of the post until it comes into contact with the insert exterior surface 130. A tip 144 of a lanyard 146 is inserted through a hole (not shown) in a side of the post 114 to a position inside the post internal bore 118. A second set screw 148 is screw threaded into the internally screw threaded bore 118 of the post and is tightened against the lanyard tip 144, thereby attaching the lanyard to the second adapter 100. As seen in FIG. 10, the lanyard tip 144 is positioned relative to the post 114 where it will not interfere with the connection of the BNC connector with the adapter. The opposite end of the lanyard is connected to a base 150 with an adhesive backing (not shown) that enables the lanyard and the adapter to be attached to the light source with which the adapter will be used. This insures that the adapter 100, although small in size, will not become lost from the light source when not in use.

The second adapter embodiment 100 is used in substantially the same manner as the first described embodiment of the adapter. The adapter sleeve 102 is first attached to the external threading 22 of the laser light source female bushing by screw threading the conductive insert 106 onto the female bushing until the end of the female bushing comes into contact with the annular stop 108 inside the sleeve. This established a circuit path from the female bushing 12 through the annular stop 108 and the conductive insert 106, the electrical device 110 and the conductive sleeve 102 of the adapter. With the adapter attached to the female busing of the laser light source, any optic fiber microsurgical instrument having the BNC connector of the invention may be easily connected and disconnected from the laser light source by turning the BNC connector one quarter turn relative to the adapter attached to the laser light source. When the BNC connector 38 of the surgical instrument is attached to the adapter 100, an electrical circuit is established from the female bushing 12 of the laser light source through the annular stop 108 and the conductive insert 106, the electrical device 110 and the adapter sleeve 102 and the collar 48 of the BNC connector. The external contact 88 of the earlier discussed laser light source is positioned to come into contact with the BNC connector 38 of the assembly and thereby a complete electrical circuit is established from the female bushing 12 of the light source through the electrical device 110 of the adapter 100 and through the BNC connector 38 and the external contact 88 of the light source.

The electrical device of either adapter, for example the resistor 68 referred to, is specifically chosen to make the adapter compatible with the particular light source. When the electric circuit discussed above is established by connecting the adapter and BNC connector of the invention with the female bushing of the light source, the light source recognizes the particular electrical device provided in the adapter. Thus, the laser light source will operate as though an SMA connector manufactured by the same manufacturer of the light source was connected to the female bushing of the light source.

Thus, the assembly of the invention including the adapter and the BNC connector enables a quick connect and disconnect of the surgical instrument with the laser light source and also enables surgical instruments to be employed with the particular light source that were not manufactured by the particular manufacturer of the light source.

While the present invention has been described by reference to a specific embodiment, it should be understood that modifications and variations of the invention may be constructed without departing from the scope of the invention defined in the following claims.

What is claimed:

1. An adapter for enabling a quick connect and disconnect between an externally threaded bushing and a BNC connector, the adapter comprising:

a cylindrical sleeve having an external surface and an internal surface, a portion of the internal surface having internal screw threading that is complementary to external screw threading of a bushing to which the sleeve is to be attached, at least one post on the external surface of the sleeve, the post being positioned to engage with a slot of a BNC connector to hold the BNC connector on the sleeve external surface;

an insulator inserted into the sleeve and the internal screw threading being on the insulator; and, a cylindrical sleeve insert mounted on the insulator inside the sleeve with the insulator separating the insert from the sleeve internal surface, the insert having an internal surface and the internal screw threading being on the insert internal surface.

2. The adapter of claim 1, further comprising:

a pair of posts are positioned on opposite sides of the sleeve exterior surface to engage with slots of a BNC connector to hold the BNC connector on the sleeve exterior surface.

3. The adapter of claim 1, further comprising:

the insert being conductive and being insulated from the sleeve by the insulator.

4. The adapter of claim 1, further comprising:

an electrical device secured inside the sleeve and being electrically connected between the sleeve and the insert.

5. The adapter of claim 1, further comprising:

an electrical device secured inside the sleeve post and being electrically connected between the sleeve and the insert.

6. An adapter for enabling a quick connect and disconnect between an externally threaded bushing and a BNC connector, the adapter comprising:

a cylindrical sleeve having an external surface and an internal surface, a portion of the internal surface having internal screw threading that is complementary to external screw threading of a bushing to which the sleeve is to be attached, at least one post on the external surface of the sleeve, the post being positioned to engage with a slot of a BNC connector to hold the BNC connector on the sleeve external surface;

an insulator inserted into the sleeve and the internal screw threading being on the insulator; and, a lanyard attached to the adapter.

7. An assembly for connecting an optic fiber instrument to an externally threaded bushing of a light source, the assembly comprising:

a BNC connector having a cylindrical collar with a center axis, the collar having at least one slot therein that spirals around the center axis of the collar;

a cylindrical sleeve adapter having a center axis, an external surface and an internal surface, a portion of the internal surface having internal screw threading that is complementary to the external screw threading of a bushing of a light source to which the sleeve is to be attached, at least one post on the sleeve positioned to engage in the slot of the BNC connector to hold the collar of the BNC connector on the external surface of the sleeve;

the cylindrical sleeve being a conductor and an insulator being inserted inside the sleeve, the insulator having an exterior surface in engagement with the sleeve interior surface and the insulator having an internal bore and the internal screw threading of the sleeve being in the internal bore of the insulator; and, a cylindrical insert mounted in the insulator internal bore with the insulator separating the insert from the sleeve interior surface, the insert having an interior surface and the internal screw threading being on the insert interior surface.

8. The assembly of claim 7, further comprising:
the collar slot being shaped to cause the collar to be attached on the external surface of the sleeve by the posts engaging in the collar slot and in response to rotating the collar one quarter turn relative to the sleeve.

9. An assembly for connecting an optic fiber instrument to an externally threaded bushing of a light source, the assembly comprising:
a BNC connector having a cylindrical collar with a center axis, the collar having at least one slot therein that spirals around the center axis of the collar;
a cylindrical sleeve adapter having a center axis, an external surface and an internal surface, a portion of the internal surface having internal screw threading that is complementary to external screw threading of a bushing of a light source to which the sleeve is to be attached, at least one post on the sleeve positioned to engage in the slot of the BNC connector to hold the collar of the BNC connector on the external surface of the sleeve;
the cylindrical sleeve being a conductor and an insulator being inserted inside the sleeve, the insulator having an exterior surface in engagement with the sleeve internal surface and the insulator having an internal bore and the internal screw threading of the sleeve being in the internal bore of the insulator;
a conductive insert secured inside the adapter sleeve and being electrically insulated from the sleeve by the insulator, the insert being positioned inside the sleeve to make electrical contact with the bushing of the light source when the adapter sleeve is threaded on the bushing of the light source; and,
an electrical device secured inside the sleeve post and being electrically connected between the sleeve and the insert.

10. An adapter for enabling a quick connect and disconnect between an externally threaded bushing of a light source and a BNC connector of an optic fiber instrument, the adapter comprising:
a cylindrical sleeve having an external surface and an internal surface, a portion of the internal surface having internal screw threading that is complementary to external screw threading of a light source bushing to which the sleeve is to be attached, at least one Post on the external surface of the sleeve, the post being positioned to engage with a slot of a BNC connector of an optic fiber instrument to hold the BNC connector on the sleeve external surface;
an electrical device secured inside the sleeve where the electrical device will be connected in an electric circuit with the light source bushing and the BNC connector when the sleeve internal screw threading is mounted on the light source bushing external screw threading and the BNC connector is mounted on the sleeve external surface; and,
the electrical device being secured inside the post of the sleeve.

11. The adapter of claim 10, further comprising:
the electrical device being electrically connected to the sleeve.

12. The adapter of claim 10, further comprising:
a conductive insert secured inside the sleeve and the electrical device being electrically connected to the conductive insert.

13. The adapter of claim 12, further comprising:
an insulator inserted into the sleeve and the conductive insert being insulated from the sleeve by the insulator.

14. The adapter of claim 12, further comprising:
the electrical device being electrically connected between the conductive insert and the sleeve.

15. An adapter for enabling a quick connect and disconnect between an externally threaded bushing of a light source and a BNC connector of an optic fiber instrument, the adapter comprising:
a cylindrical sleeve having an external surface and an internal surface, a portion of the internal surface having internal screw threading that is complementary to external screw threading of a light source bushing to which the sleeve is to be attached, at least one Post on the external surface of the sleeve, the post being positioned to engage with a slot of a BNC connector of an optic fiber instrument to hold the BNC connector on the sleeve external surface;
an electrical device secured inside the sleeve where the electrical device will be connected in an electric circuit with the light source bushing and the BNC connector when the sleeve internal screw threading is mounted on the light source bushing external screw threading and the BNC connector is mounted on the sleeve external surface;
a conductive insert secured inside the sleeve and the electrical device being electrically connected to the conductive insert;
an insulator inserted into the sleeve and the conductive insert being insulated from the sleeve by the insulator; and,
the internal screw threading being on the conductive insert.

16. An adapter for enabling a quick connect and disconnect between an externally threaded bushing of a light source and a BNC connector of an optic fiber instrument, the adapter comprising:
a cylindrical sleeve having an external surface and an internal surface, a portion of the internal surface having internal screw threading that is complementary to external screw threading of a light source bushing to which the sleeve is to be attached, at least one Post on the external surface of the sleeve, the post being positioned to engage with a slot of a BNC connector of an optic fiber instrument to hold the BNC connector on the sleeve external surface;
an electrical device secured inside the sleeve where the electrical device will be connected in an electric circuit with the light source bushing and the BNC connector when the sleeve internal screw threading is mounted on the light source bushing external screw threading and the BNC connector is mounted on the sleeve external surface;
a conductive insert secured inside the sleeve and the electrical device being electrically connected to the conductive insert; and,
a lanyard attached to the adapter.

17. An assembly for connecting an optic fiber instrument to an externally threaded bushing of a light source, the assembly comprising:
a BNC connector having a cylindrical collar with a center axis, the collar having at least one slot therein that spirals around the center axis of the collar;
a cylindrical sleeve adapter having a center axis, an external surface and an internal surface, a portion of the internal surface having internal screw threading that is complementary to external screw threading of a bushing of a light source to which the sleeve is to be attached, at least one post on the sleeve positioned to engage in the slot of the BNC connector to hold the collar of the BNC connector on the external surface of the sleeve;

an electrical device secured inside the sleeve; and, the electrical device being secured inside the post of the sleeve.

18. The assembly of claim 17, further comprising:

the electrical device being electrically connected to the sleeve.

19. An assembly for connecting an optic fiber instrument to an externally threaded bushing of a light source, the assembly comprising:

a BNC connector having a cylindrical collar with a center axis, the collar having at least one slot therein that spirals around the center axis of the collar;

a cylindrical sleeve adapter having a center axis, an external surface and an internal surface, a portion of the internal surface having internal screw threading that is complementary to external screw threading of a bushing of a light source to which the sleeve is to be attached, at least one post on the sleeve positioned to engage in the slot of the BNC connector to hold the collar of the BNC connector on the external surface of the sleeve;

an electrical device secured inside the sleeve;

a conductive insert secured inside the sleeve and the electrical device being electrically connected to the conductive insert;

an insulator inserted into the sleeve and the conductive insert being insulated from the sleeve by the insulator; and, the internal screw threading being on the conductive insert.

20. The assembly of claim 19 further comprising:

the electrical device being electrically connected between the conductive insert and the sleeve.

* * * * *